US009880670B2

United States Patent
Friese et al.

(10) Patent No.: US 9,880,670 B2
(45) Date of Patent: Jan. 30, 2018

(54) GESTURE CONTROL HAVING AUTOMATED CALIBRATION

(71) Applicant: SIEMENS AKTIENGESELLSCHAFT, München (DE)

(72) Inventors: Thomas Friese, München (DE); Thomas Goβler, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 186 days.

(21) Appl. No.: 14/781,997

(22) PCT Filed: Jan. 15, 2014

(86) PCT No.: PCT/EP2014/050731
§ 371 (c)(1),
(2) Date: Oct. 2, 2015

(87) PCT Pub. No.: WO2014/166645
PCT Pub. Date: Oct. 16, 2014

(65) Prior Publication Data
US 2016/0041693 A1   Feb. 11, 2016

(30) Foreign Application Priority Data

Apr. 12, 2013   (DE) .................. 10 2013 206 569

(51) Int. Cl.
*H04N 5/225*   (2006.01)
*G06F 3/042*   (2006.01)
(Continued)

(52) U.S. Cl.
CPC ............ *G06F 3/0425* (2013.01); *G06F 3/017* (2013.01); *G06F 3/0304* (2013.01);
(Continued)

(58) Field of Classification Search
CPC ...... G06F 3/017; G06F 3/0304; G06F 3/0346; G06F 3/0412; G06F 3/0418
(Continued)

(56) References Cited

U.S. PATENT DOCUMENTS 6,750,848 B1   6/2004   Pryor
7,834,847 B2   11/2010  Boillot et al.
(Continued)

FOREIGN PATENT DOCUMENTS

CN   101785056 A   7/2010
CN   102156859 A   8/2011
(Continued)

OTHER PUBLICATIONS

Auf dem Weg zum Natural User Interface (Teil 3)—Die Spielekonsole im OP, chrome://firefoxreader/content/print. html?1351696451642, 2012.
(Continued)

*Primary Examiner* — Helen Shibru
(74) *Attorney, Agent, or Firm* — Lempia Summerfield Katz LLC

(57) ABSTRACT

A basis image is captured by an image capture device and transmitted to a computing unit. A gesture of a user of the computing unit is identified by the computing unit based on the basis image. An action is determined and executed by the computing unit depending on the identified gesture. The action is determined by the computing unit for at least one of the gestures in addition in dependence on a relative position of the image capture device relative to a display device. No later than upon capturing the basis image, an additional image is captured by at least one additional image capture device and transmitted to the computing unit. On the basis of the additional image, the relative position of the
(Continued)

image capture device relative to the display device is determined by the computing unit.

18 Claims, 1 Drawing Sheet

(51) Int. Cl.
 G06F 3/01 (2006.01)
 G06F 3/03 (2006.01)
 G06F 3/0346 (2013.01)
 G06F 3/041 (2006.01)
 A61B 17/00 (2006.01)

(52) U.S. Cl.
 CPC .......... *G06F 3/0346* (2013.01); *G06F 3/0412* (2013.01); *G06F 3/0418* (2013.01); *A61B 2017/00207* (2013.01); *G06F 2203/04808* (2013.01)

(58) Field of Classification Search
 USPC .......................................................... 348/169
 See application file for complete search history.

(56) References Cited

U.S. PATENT DOCUMENTS

| | | | |
|---|---|---|---|
| 8,612,641 B1* | 12/2013 | Bozarth | G06F 3/0227 710/15 |
| 9,223,404 B1* | 12/2015 | Ivanchenko | G06T 7/11 |
| 2003/0190076 A1* | 10/2003 | DeLean | G06F 21/32 382/209 |
| 2004/0176925 A1 | 9/2004 | Satoh et al. | |
| 2007/0125633 A1 | 6/2007 | Boillot | |
| 2008/0069405 A1 | 3/2008 | Endo et al. | |
| 2010/0013764 A1 | 1/2010 | Gu et al. | |
| 2011/0029913 A1 | 2/2011 | Boillot et al. | |
| 2011/0033650 A1 | 2/2011 | Kitsunai et al. | |
| 2011/0090147 A1 | 4/2011 | Gervais et al. | |
| 2012/0293405 A1* | 11/2012 | Iida | H04N 5/64 345/156 |
| 2013/0090166 A1 | 4/2013 | Mao et al. | |
| 2013/0141324 A1* | 6/2013 | Zambrano | G06F 3/011 345/156 |
| 2013/0176337 A1 | 7/2013 | Lu | |
| 2014/0267405 A1* | 9/2014 | Mullins | G06T 19/006 345/633 |
| 2014/0337802 A1* | 11/2014 | Bertsch | G06F 3/04815 715/848 |
| 2017/0161903 A1* | 6/2017 | Yerli | G06T 7/0046 |

FOREIGN PATENT DOCUMENTS

| | | |
|---|---|---|
| CN | 102446048 A | 5/2012 |
| CN | 102918476 A | 2/2013 |
| EP | 1739622 A2 | 1/2007 |
| WO | WO0016121 A1 | 3/2000 |
| WO | WO2004055776 A1 | 7/2004 |
| WO | WO2004057450 A1 | 7/2004 |
| WO | WO2011085815 A1 | 7/2011 |
| WO | WO2012129669 A1 | 10/2012 |

OTHER PUBLICATIONS

German Office action for related German Application No. 10 2013 206 569.8, dated Nov. 8, 2013, with English Translation.
Matthias Hohensee, Die Gestensteuerung erorbert Büros, Kinect—Digitale Welt—Technologie . . . , Wirschaftswoche, 4 pages, http://www.wiwo.de/technologie/digitale-welt/kinect-die gestensteuerung, 2012.
PCT International Search Report and Written Opinion of the International Searching Authority dated May 9, 2014 for corresponding PCT/EP2014/050731.
Chinese Office Action for related Chinese Application No. 2014 800 206 30.3 dated May 22, 2017, with English Translation.

* cited by examiner

GESTURE CONTROL HAVING AUTOMATED CALIBRATION

RELATED CASES

The present patent document is a §371 nationalization of PCT Application Serial Number PCT/EP2014/050731, filed Jan. 15, 2014, designating the United States, which is hereby incorporated by reference. This patent document also claims the benefit of DE 10 2013 206 569.8, filed Apr. 12, 2013, which is also hereby incorporated by reference.

BACKGROUND

The present embodiments to a method of control for a computing unit, wherein a basis image is captured by an image capture device and is communicated to the computing unit. The computing unit determines, by reference to the basis image, a gesture by a user of the computing unit. The computing unit determines an action that depends on the detected gesture, and the action is executed.

The present embodiments also relate in addition to a computer facility. The computer facility incorporates an image capture device, a display device and a computing unit. The computing unit is linked to the image capture device and to the display device for the purpose of exchanging items of data. A basis image is captured by the image capture device and is communicated to the computing unit. The computing unit determines, by reference to the basis image, a gesture of a user of the computing unit. The computing unit determines an action that depends on the detected gesture, and the action is executed.

Control methods of this type and computer facilities of this type are generally known. Purely by way of example, see WO 2011/085815 A1, US 2010/013764 A1, US 2011/029913 A1, US 2011/090147 A1 and U.S. Pat. No. 7,834,847 B2.

Contactless interaction with computer facilities is a clear trend in the context of so-called natural input methods (NUI=Natural User Input). This applies both in information processing in general and also in particular in the medical field. Thus, contactless interaction is being used, for example, in operating theaters, in which the doctor performing the operation wishes to view operation-related images of the patient during the operation. In this case, for reasons of sterility, the operating doctor may not touch the usual interaction devices on the computer (e.g., a computer mouse, a keyboard or a touchscreen). It must nevertheless be possible to control the display device. In particular, it must be possible to control which image is shown on the display device. In general, it must also be possible to operate control buttons and the like on the display device.

A known approach is that someone other than the operating doctor operates the usual interaction facilities, on the basis of appropriate instructions from the doctor. This is unreliable, costs valuable time and often leads to communication problems between the operating doctor and the other person. Gesture control represents a valuable advantage. With gesture control, a so-called range image is generally determined (i.e. an image in which each point in an image which is per se two-dimensional has assigned to it in addition an item of data about the third direction in three-dimensional space). The capture and evaluation of such range images is known per se. Range images of this type may be captured, for example, by two normal cameras that together supply a stereoscopic image. Alternatively, it is possible to project a sinusoidally modulated pattern in the space and, by reference to distortions in the sinusoidally modulated pattern, to determine the range information.

For gesture recognition to work correctly, it is in many cases necessary that the relative position of the image capture device relative to the display device is known. In the state of the art, the absolute positions of the image capture device and the display device are therefore established beforehand. After this, a calibration operation is carried out, in which the relative position of the image capture device relative to the display device is determined. After this calibration, the relative position of the image capture device relative to the display device may then no longer be changed. In particular, a change in the relative position of the image capture device relative to the display device is not desired in ongoing operation.

The requirement that the relative position of the image capture device relative to the display device may no longer be changed after the calibration represents a significant restriction in practice. It is instead desirable to be able to change the relative position of the image capture device relative to the display device at any time—even in ongoing operation.

From WO2004/055 776 A1, a method of control for a computing unit is known. A basis image is captured by an image capture device and is communicated to the computing unit. The computing unit, by reference to the basis image, identifies a gesture by a user of the computing unit and determines an action that depends on the gesture identified. The action is carried out.

SUMMARY AND DETAILED DESCRIPTION

The scope of the present invention is defined solely by the appended claims and is not affected to any degree by the statements within this summary.

The relative position of the image capture device relative to the display device may be changed, even in ongoing operation, without having a negative influence on the functional integrity of gesture recognition. In particular, time-consuming manual calibration may not be needed.

In accordance with one embodiment, a method of control of the type mentioned in the introduction is formed in that, at the latest when the basis image is being captured, a supplementary image is captured by at least one further image capture device and is communicated to the computing unit. By reference to the supplementary image, the computing unit determines the relative position of the image capture device relative to the display device.

By this supplementary image, it becomes possible to keep the relative position of the image capture device relative to the display device continuously up to date within the computing unit during ongoing operation.

In one preferred embodiment of the method of control, the further image capture device is arranged in a fixed location. This embodiment may be realized particularly easily.

In the case where the further image capture device is in a fixed location, the computing unit preferably determines, by reference to the at least one supplementary image, an absolute position of the image capture device relative to a fixed-location coordinate system and an absolute position of the display device relative to the fixed-location coordinate system. By reference to the absolute positions of the image capture device and the display device, the computing unit then determines the relative position of the image capture device relative to the display device.

In a further preferred embodiment of the method of control, the image capture device and/or the display device are movable. For example, the image capture device and/or the display device may be affixed to a ceiling via movable carrier arms, which may possibly originate at a common bearing structure.

The time points at which the computing unit determines the relative position of the image capture device relative to the display device may be specified as required. It is, for example, possible that the computing unit determines the relative position of the image capture device relative to the display device continuously, at fixed intervals of time, when initiated by a user command, or when initiated by a change of an absolute position of the image capture device, detected by a sensing system, relative to a fixed-location coordinate system, of an absolute position of the display device relative to a fixed-location coordinate system, or of the relative position of the image capture device relative to the display device.

The action determined and performed by the computing unit may also be defined as required. Preferably, however, the action will be to control the display device.

In accordance with another embodiment, a computer facility of the type cited in the introduction will be of a form such that, the computer facility incorporates (in addition to the image capture device) at least one further image capture device. The computing unit is also linked to the at least one further image capture device for the purpose of exchanging items of data. At the latest when the basis image is captured, at least one supplementary image is captured by the further image capture device and is communicated to the computing unit. By reference to the at least one supplementary image, the computing unit determines the relative position of the image capture device relative to the display device.

The advantageous embodiments of the computer facility correspond to those of the method of control.

BRIEF DESCRIPTION OF THE DRAWINGS

The characteristics, features and advantages of this invention described above, together with the manner in which these are achieved, will be more clearly and evidently understandable in conjunction with the following description of the exemplary embodiments, which will be explained in more detail in conjunction with the drawings. These show as schematic diagrams.

DETAILED DESCRIPTION

Figure 1:
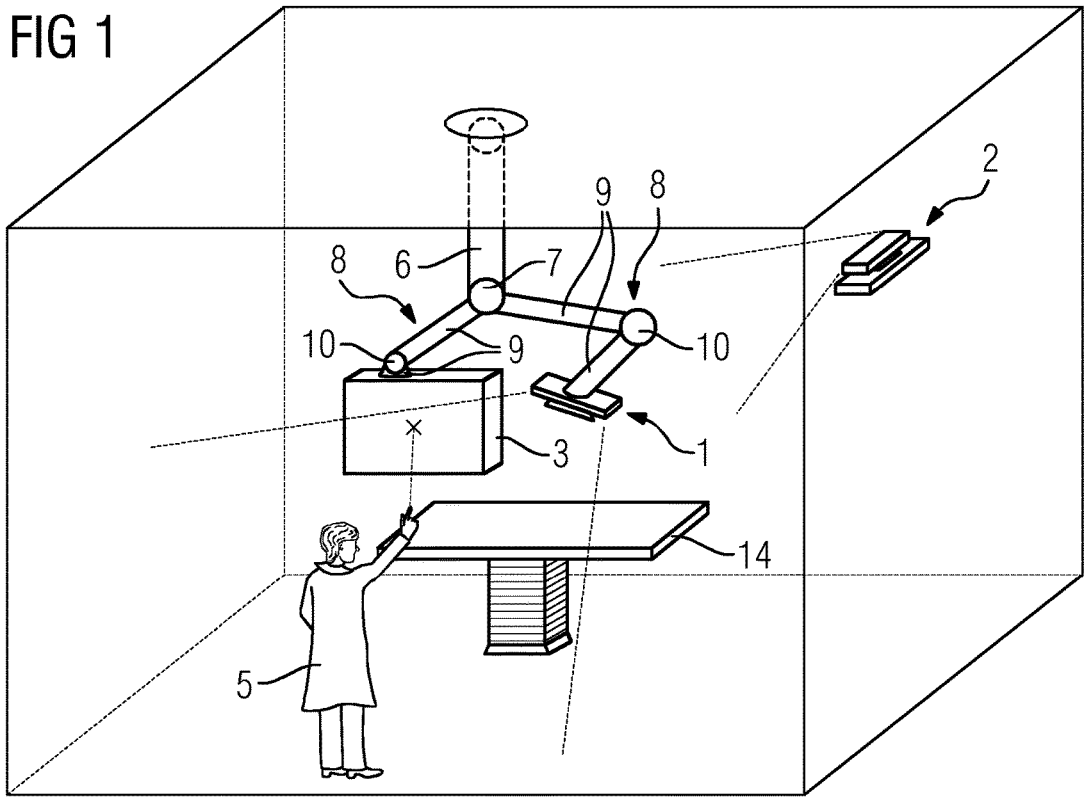
FIG. 1 is a perspective view of a space in which is arranged a computer facility.
Figure 2:
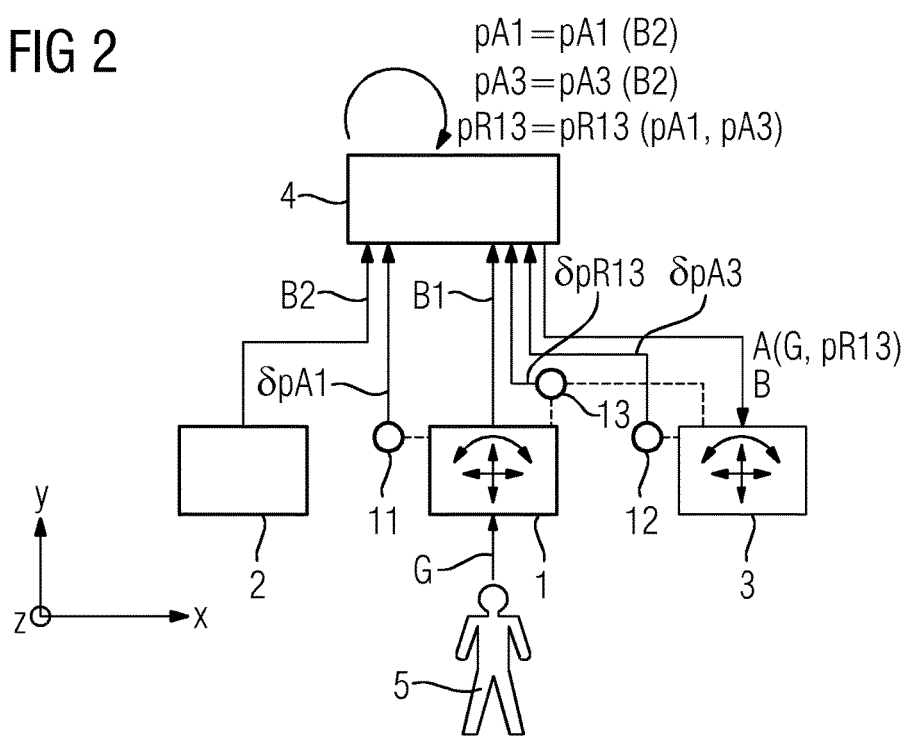
FIG. 2 is a block diagram of the computer facility in FIG. 1.

As shown in FIGS. 1 and 2, a computer facility incorporates an image capture device 1, at least one further image capture device 2, a display device 3 and a computing unit 4. The image capture device 1, the at least one further image capture device 2 and the display device 3 are linked to the computing unit 4 for the purpose of exchanging items of data. In particular, a basis image B1 is captured by the image capture device 1 and is communicated to the computing unit 4. In an analogous way, a supplementary image B2 (or, in the case when there are several further image capture devices 2, a supplementary image B2 from each further image capture device 2) is captured and communicated to the computing unit 4 by the further image capture device 2. The images B1, B2 captured by the image capture devices 1, 2 are evaluated by the computing unit 4. Depending on the result of the evaluation, the computing unit 4 may, for example, actuate the display device 3.

The computing unit 4 may be in the form of a common PC, a workstation or similar computing unit. The display device 3 can be in the form of a common computer display, for example, an LCD display or a TFT display.

Relative to the display device 3, the image capture device 1 has a relative position pR13. This relative position pR13 is relative to a coordinate system that is fixed relative to the display device 3. The relative position pR13 may include translational and/or rotational components.

The image capture device 1, the display device 3 and the computing unit 4 work together as follows:

The image capture device 1 captures the basis image B1 and communicates the basis image B1 to the computing unit 4. The basis image B1 that has been captured shows (among other things) a user 5 of the computing unit 4. By reference to the basis image B1, the computing unit identifies a gesture G from the user 5. For example, the computing unit 4 may evaluate the basis image B1 in terms of whether the user 5 is raising one hand or both hands, whether the user claps hands once or twice, whether the user points in a particular direction with an arm and/or a finger, and many similar possibilities. Of course, the identification of other or additional gestures G is also possible. For the purpose of clear recognition of the gesture G, special markings may be arranged on the user 5. For example, the user 5 may wear special gloves. However, this is not absolutely essential.

For the reliable evaluation of the basis image B1 by the computing unit 4 (i.e., for reliable recognition of the gesture G concerned), it is of advantage if the basis image B1 is a so-called range image (i.e., that the (two-dimensionally spatially resolved) individual pixels of the range image are assigned a range value), if necessary in addition to their image data value. The range characterizes a distance, from the image capture device 1, assigned to the pixel concerned. The capture of this type of range image is known per se to persons skilled in the art. For example, the image capture device 1 may incorporate several individual image sensors, which capture the scene to be recorded from various viewing angles. It is also possible, by a suitable light source, to project a pattern of stripes (or some other pattern) into the space that is recorded by the image capture device 1. By reference to the distortions in the pattern, the relevant distance in the basis image B1 captured by the image capture device 1 is determined.

If the computing unit 4 has recognized a gesture G, the computing unit 4 determines an action A that depends on the gesture G that has been identified, and carries out the action A. The computing unit 4 is thus controlled by the gesture G and the associated action A.

It is possible that for some of the gestures G, the action A determined is independent of other parameters. For example, a double clap of the hands by the user 5 may be interpreted in the sense of a end-command, on the basis of which further interaction between the image capture device 1 and the computing unit 4 is terminated. It is also possible that the action A depends on other parameters, which are connected with other matters than the basis image B1 captured by the image capture device 1. For example, a linkage may be effected between a gesture G and a voice command spoken by the user 4. Other approaches are also possible.

In many cases, however, the action A determined by the computing unit 4 will depend also—in addition to depending on the gesture G per se—on the relative position pR13. This is especially required when the action A determined and carried out by the computing unit 4 is a control action for the display device 3. However, it is possible that the particular action A determined depends on the relative position pR13, even if the action A that is determined and carried out is not an action to control the display device 3.

It is possible that the dependence of the action A additionally also on the relative position pR13 only applies to an individual, quite specific, gesture G. Alternatively, it is possible that the dependence of the Action A also on the relative position pR13 applies for several gestures G or even for all gestures G. Explained below—purely by way of examples—are a few possible gestures G, for which their associated action A may also depend on the relative position pR13.

For example, if the user 5 points with one of his arms or with a finger in a particular direction, this pointing may be interpreted by the computing unit 4 as the selection of a particular element that lies in the direction in which the user 5 is pointing. The particular element may be, in particular, an element that is shown on the display device 3. Alternatively or additionally, it is for example possible that a section of an image B (this image has nothing to do with the basis image B1, and also nothing to do with the supplementary image B2) shown on the display device 3 is displaced, wherein at least the direction of the displacement depends on the direction in which the user 5 moves one of his arms or one of his hands. In addition, the extent of the displacement may possibly depend on the speed and/or extent of this movement. It is also possible, for example in a way similar to leafing through the pages of a book, to select, from a sequence of images B (these images again have nothing to do with the basis image B1, and also nothing to do with the supplementary image B2), a preceding or following image B in the sequence, and to show it via the display device 3. In this case, the direction of the leafing may, for example, depend on the direction of movement of the arms or hands of the user 5. Other actions A that depend on the relative position pR13 are also possible. As mentioned, the above examples are purely by way of example.

In cases of this type, that is if the action A that is determined and carried out depends on the relative position pR13, the relative position pR13 must thus be known to the computing unit 4. It is for this purpose that the at least one further image capture device 2 is present. In what follows, it is presumed that only one single further image capture device 2 is present. However, there could equally well also be several further image capture devices 2 present, each capturing a supplementary image B2.

The further image capture device 2 captures the supplementary image B2 at the latest when the basis image B1 is captured. Preferably, the capture and communication will take place before the basis image B1 is captured. However, simultaneous capture and communication are also possible. The further image capture device 2 communicates the supplementary image B2 to the computing unit 4. The computing unit 4 evaluates the supplementary image B2. In particular, the computing unit 4 determines, by reference to the supplementary image B2, the relative position pR13 of the image capture device 1 relative to the display device 3.

For the reliable evaluation of the supplementary image B2 by the computing unit 4 (i.e. for reliable determination of the relative position pR13), the further image capture device 2 is arranged in such a way that the supplementary image B2 contains the image capture device 1 and the display device 3. For a particularly reliable evaluation of the supplementary image B2, it may in some circumstances be logical to arrange special markings on the image capture device 1 and/or on the display device 3.

In many cases, it may be sufficient if the further image capture device 2 is not rigidly mounted but for its part is arranged on a holder that is translationally and/or rotationally movable. Preferably however, the further image capture device 2 will be arranged in a fixed location, corresponding to the diagram in FIG. 1.

For a reliable evaluation of the supplementary image B2 by the computing unit 4, it is of further advantage if the supplementary image B2 is a so-called range image. The embodiments set out above for the basis image B1 may thus also be applied in an analogous manner to the supplementary image B2.

Particularly, in the case that the further image capture device 2 is arranged to have a fixed location, the evaluation of the supplementary image B2 by the computing unit 4 may be undertaken as follows, for example: the computing unit 4 determines, by reference to the supplementary image B2, an absolute position pA1 for the image capture device 1. This absolute position pA1 is relative to a coordinate system with a fixed location (e.g., relative to the space in which the image capture device 1 and the display device 3 are arranged). The fixed-location coordinate system may be defined, for example, in Cartesian coordinates x, y, z. In an analogous way, the computing unit 4 determines, by reference to the supplementary image B2, an absolute position pA3 for the display device 3. This absolute position pA3 is also relative to the fixed-location coordinate system. Using the two absolute positions pA1 and pA3, the computing unit 4 then determines the relative position pR13 of the image capture device 1 relative to the display device 3.

It is possible in principle that the image capture device 1 and the display device 3, as in the case of the further image capture device 2, are fixed-location facilities. However, the present embodiments show strength in full if the image capture device 1 and/or the display device 3 are movable. Here, it is possible, depending on the embodiment, that only the one or only the other of the two devices 1, 3 is movable. Equally it is possible, depending on the construction, for both the devices 1, 3 to be movable. Depending on the construction, the movements of the two devices 1, 3 may be coupled to each other or independent of one another. It is preferable that the two devices 1, 3 may move independently of each other. One possible realization of the independent movability of the image capture device 1 and the display device 3 is explained below in more detail, making reference to FIG. 1. The corresponding embodiments are, however, purely by way of example. Other possible forms of movability may be realized.

As shown in FIG. 1, a bearing structure 6 that projects downward is affixed to a ceiling of the space. This bearing structure 6 has an articulation 7, from which (at least) two carrier arms 8 emerge. The carrier arms 8 may be rigid. Alternatively, the carrier arms 8 may in turn have several component elements 9 which are linked to each other by further articulations 10. Suspensions of this type are familiar.

In the form explained above in conjunction with FIG. 1, the user 5 may position the display device 3, at least up-and-down and sideways, by appropriate repositioning of the associated carrier arm 8. In an analogous way, the user 5 may, by appropriate repositioning of the associated carrier arm 8, position the image capture device 1, at least up-and-down and sideways. Under some circumstance, it is also possible to effect positioning in the depth direction and/or by rotational movements. It is preferable if these two positioning possibilities may be realized separately from each other.

Alternatively, it is possible that the positioning possibilities are linked to each other. For example, the carrier arms 8 may work together with each other in the region of the articulation 7, so that in the articulation 7 the carrier arms 8 may only ever be repositioned by the same angle but in opposite rotational directions.

If the relative position pR13 of the image capture device 1 changes relative to the display device 3, the relative position pR13 is redetermined. Otherwise, there would be a danger of a faulty determination of the action A. In order to exclude this danger, that is in order to always evaluate the current and real relative position pR13 in the computing unit 4, various embodiments are possible.

It is for example possible that the supplementary image B2 is captured by the further image capture device 2 at fixed intervals of time and/or is evaluated by the computing unit 4 at fixed intervals of time. For example, an evaluation at time intervals of 15 seconds, 1 minute, 10 minutes, 1 hour etc. would be possible. The time interval may be permanently prescribed. Alternatively, the time interval may be prescribed to the computing unit 4 by the user 5.

Alternatively, it is possible that the supplementary image B2 is only captured by the further image capture device 2, and/or is only evaluated by the computing unit 4, if an appropriate user command is issued to the computing unit 4 by the user 5. For example, the user 5 may issue an appropriate voice command or (preferably by part of the body other than his hands, for example using an elbow or a foot) activates a switch or button.

As yet another alternative, it is possible that the supplementary image B2 is captured by the further image capture device 2 when the computer facility is switched on and/or is evaluated by the computing unit 4 when the computer facility is switched on.

As yet another alternative, it is possible that a sensing system 11, 12, 13 is assigned to the image capture device 1 and/or to the display device 3. The sensing system 11, 12, 13 recognizes a change δpA1, δpA3 in the absolute positions pA1, pA3 or a change δpR13 in the relative position pR13. In this case, the recognition of a change δpA1, δpA3 in one of the absolute positions pA1, pA3 or of both absolute positions pA1, pA3 and/or the recognition of a change δpR13 in the relative position pR13 could initiate the detection and evaluation of the supplementary image B2.

The possibilities cited above as to the time points and/or the events which initiate a determination of the relative position pR13 may be combined with each other as required.

Alternatively, it is possible that the supplementary image B2 is continuously captured by the further image capture device 2 and communicated to the computing unit 4. In this case, the determination of the current relative position pR13 at the computing unit 4 may also take place continuously.

The present embodiments may in principle be used in any desired environment. Preferably however, the present embodiments are used in a medical area. In this case, the space in which the image capture device 1, the further image capture device 2 and the display device 3 are arranged may in particular be in the form of an operating theater. This is indicated in FIG. 1 by the schematic diagram of an OP table 14.

In the context of the present embodiments, the determination of the relative position pR13 of the image capture device 1 relative to the display device 3 has been gone into in detail above. Insofar as necessary, it is possible to determine, in addition to the relative position pR13 of the image capture device 1 relative to the display device 3, an absolute position of the user 5 relative to the fixed-location coordinate system and/or to undertake a determination of the relative position of the user 5 relative to the image capture device 1 and/or a relative position of the user 5 relative to the display device 3. In respect of the user 5, other more extensive evaluations are also possible, such as for example the determination of their height.

The present embodiments have many advantages. In particular, it is possible in a simple and reliable way to undertake at any time as required a calibration of the gesture control, that is the determination of the relative position pR13 of the image capture device 1 relative to the display device 3.

Although the invention has been illustrated and described in more detail by the preferred exemplary embodiment, the invention is not restricted by the examples disclosed and other variations can be derived from them by a person skilled in the art without going outside the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method of control for a computing unit, the method comprising:
   capturing a basis image by an image capture device
   communicating the basis image to the computing unit,
   determining, by the computing unit, by reference to the basis image, a gesture by a user of the computing unit,
   determining, by the computing unit, an action that depends on the detected gesture,
   executing the action as a control of the computing unit,
   determining, for at least the gesture and by the computing unit, the action as a function of a relative position of the image capture device relative to a display device in addition to the detected gesture, the relative position known to the computer unit in determining the action,
   capturing, at the latest when the basis image is being captured, a supplementary image by at least one further image capture device,
   communicating the supplementary image to the computing unit, and
   determining, by reference to the at least one supplementary image and by the computing unit, the relative position of the image capture device relative to the display device.

2. The method of control as claimed in claim 1, further comprising fixing a location of the further image capture device.

3. The method of control as claimed in claim 2, wherein determining the relative position comprises the computing unit determining, by reference to the at least one supplementary image, an absolute position for the image capture device relative to a fixed-location coordinate system and an absolute position for the display device relative to a fixed-location coordinate system and, by reference to the absolute positions of the image capture device and of the display device, the relative position of the image capture device relative to the display device.

4. The method of control as claimed in claim 1, further comprising moving the image capture device and/or the display device.

5. The method of control as claimed in claim 1, wherein the relative position of the image capture device relative to the display device is determined continuously, at fixed intervals of time, when initiated by a user command, or when initiated by a change recognized by a sensing system of an absolute position of the image capture device relative to a fixed-location coordinate system, a change of an absolute position of the display device relative to a fixed-location coordinate system, or a change of the relative position of the image capture device relative to the display device.

6. The method of control as claimed in claim 1, further comprising controlling the display device with the action.

7. A computer facility comprising:
an image capture device,
at least one further image capture device,
a display device, and
a computing unit,
wherein the computing unit is linked to the image capture device, to the at least one further image capture device, and to the display device for exchanging items of data,
wherein the image capture device is configured to capture a basis image and communicate the basis image to the computing unit,
wherein the computing unit is configured to determine, by reference to the basis image, a gesture of a user of the computing unit,
wherein the computing unit is configured to determine an action that depends on the gesture and to execute the action,
wherein, for at least the gesture, the computing unit is configured to determine the action from, in addition to the gesture, a relative position of the image capture device relative to the display device,
wherein the at least one further image capture device is configured to capture, at the latest when the basis image is being captured, a supplementary image and is configured to communicate the supplementary image to the computing unit,
wherein, by reference to the supplementary image, the computing unit is configured to determine the relative position of the image capture device relative to the display device.

8. The computer facility as claimed in claim 7, wherein the further image capture device has a fixed location.

9. The computer facility as claimed in claim 8, wherein the computing unit is configured to determine, by reference to the at least one supplementary image, an absolute position for the image capture device relative to the fixed-location coordinate system and an absolute position for the display device relative to the fixed-location coordinate system and, by reference to the absolute positions of the image capture device and of the display device, is configured to determine the relative position of the image capture device relative to the display device.

10. The computer facility as claimed in claim 7, wherein the image capture device and/or the display device are movable.

11. The computer facility as claimed in claim 7, wherein the computing unit is configure to determine the relative position of the image capture device relative to the display device continuously, at fixed intervals of time, when initiated by a user command, or when initiated by a change recognized by a sensing system of an absolute position of the image capture device relative to a fixed-location coordinate system, of an absolute position of the display device relative to a fixed-location coordinate system, or of the relative position of the image capture device relative to the display device.

12. The computer facility as claimed in claim 7, wherein the action is a control action for the display device.

13. The computer facility as claimed in claim 9, wherein the image capture device and/or the display device are movable.

14. The computer facility as claimed in claim 13, wherein the computing unit is configure to determine the relative position of the image capture device relative to the display device continuously, at fixed intervals of time, when initiated by a user command, or when initiated by a change recognized by a sensing system of the absolute position of the image capture device relative to a fixed-location coordinate system, of the absolute position of the display device relative to a fixed-location coordinate system, or of the relative position of the image capture device relative to the display device.

15. The computer facility as claimed in claim 13, wherein the action is a control action for the display device.

16. The method of control as claimed in claim 3 further comprising moving the image capture device and/or the display device.

17. The method of control as claimed in claim 16, wherein the relative position of the image capture device relative to the display device is determined continuously, at fixed intervals of time, when initiated by a user command, or when initiated by a change-recognized by a sensing system of the absolute position of the image capture device relative to a fixed-location coordinate system, a change of the absolute position of the display device relative to a fixed-location coordinate system, or a change of the relative position of the image capture device relative to the display device.

18. The method of control as claimed in claim 3, further comprising controlling the display device with the action.

* * * * *